United States Patent

Starkweather

[11] Patent Number: 5,836,971
[45] Date of Patent: Nov. 17, 1998

[54] DYNAMIC REZONING OF A TIERED THERAPY INPLANTABLE CARDIOVERTER DEFIBRILLATOR/PACEMAKER (ICD) DEVICE

[75] Inventor: Timothy J. Starkweather, Boulder Creek, Calif.

[73] Assignee: Pacesetter, Inc., Sylmar, Calif.

[21] Appl. No.: 806,960

[22] Filed: Feb. 26, 1997

[51] Int. Cl.[6] .................................................. A61N 1/39
[52] U.S. Cl. ................................................. 607/4; 607/14
[58] Field of Search .................................. 607/4, 5, 7, 14; 128/702, 705; 600/515, 518

[56] References Cited

U.S. PATENT DOCUMENTS

| | | |
|---|---|---|
| 4,295,474 | 10/1981 | Fischell . |
| 4,300,567 | 11/1981 | Kolenik et al. . |
| 4,384,585 | 5/1983 | Zipes . |
| 4,693,253 | 9/1987 | Adams . |
| 4,712,555 | 12/1987 | Thornander et al. . |
| 4,787,389 | 11/1988 | Tarjan . |
| 4,809,697 | 3/1989 | Causey et al. . |
| 4,830,006 | 5/1989 | Haluska et al. ............................. 607/5 |
| 4,940,052 | 7/1990 | Mann et al. . |
| 4,969,465 | 11/1990 | Pless et al. ................................. 607/14 |
| 4,989,602 | 2/1991 | Sholder et al. . |
| 5,318,591 | 6/1994 | Causey et al. . |
| 5,350,402 | 9/1994 | Infinger et al. . |
| 5,425,749 | 6/1995 | Adams . |
| 5,470,342 | 11/1995 | Mann et al. . |

Primary Examiner—William E. Kamm
Assistant Examiner—George R. Evanisko

[57] ABSTRACT

An implantable cardioverter/defibrillator/pacemaker (ICD) device having tiered level therapies, detects an arrhythmia through an electrode adapted to be coupled to a patient's heart. An output capacitor is coupled to the electrode through an output switch. A charging circuit, coupled to the output capacitor, charges the output capacitor to a programmed energy level. A control circuit, coupled to the charging circuit and the output switch, generates control signals to control the charging of the output capacitor and the closure of the output switch in accordance with a prescribed tiered therapy. The control circuit dynamically adjusts the rate zone boundaries, prior to a subsequent arrhythmia redetection, to include all lower rate zones into a current rate zone; and, in the event that the last programmed shock of the current rate zone has been delivered, the control circuit also dynamically readjusts the rate zone boundaries, prior to a subsequent arrhythmia redetection, to include the current rate zone in a higher rate zone.

21 Claims, 5 Drawing Sheets

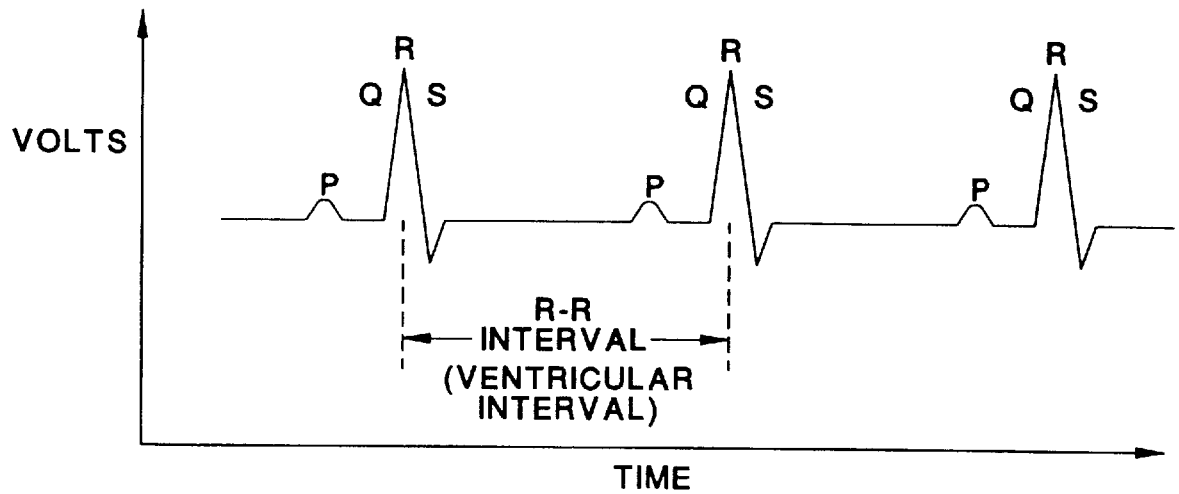
FIG. 2
| RATE ZONE | LOWER LIMIT | UPPER LIMIT |
|---|---|---|
| VF | ≥240 BPM | |
| VT2 | ≥200 BPM | <240 BPM |
| VT1 | ≥150 BPM | <200 BPM |
ARRHYTHMIA RATE ZONE CLASSIFICATIONS
FIG. 3
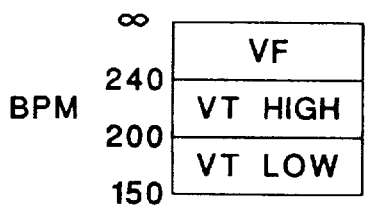
INITIAL DETECTION IN VT HIGH RATE ZONE
FIG. 4A
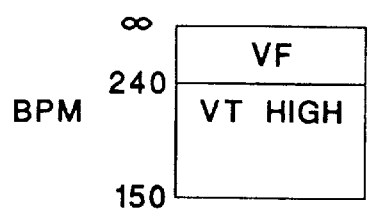
"PULL-UP" VT LOW (ALL LOWER RATE ZONES) INTO VT HIGH RATE ZONE
FIG. 4B

DYNAMIC REZONING OF A TIERED THERAPY INPLANTABLE CARDIOVERTER DEFIBRILLATOR/PACEMAKER (ICD) DEVICE

FIELD OF THE INVENTION

The present invention relates to implantable medical devices and methods, and more particularly to implantable cardioverter defibrillator/pacemaker (ICD) techniques capable of dynamically rezoning rate-zone boundaries that correspond to tiered level therapies. Such dynamic rezoning of rate-zone boundaries ensures, for example, that a shock delivered to a patient's heart is never immediately followed by a shock of lower energy, and further assumes that such shock, if unsuccessful at terminating the arrhythmia, is followed by a subsequent shock in a timely manner.

BACKGROUND OF THE INVENTION

The primary function of an implantable cardioverter defibrillator/pacemaker (ICD) device is to sense the occurrence of a cardiac arrhythmia, i.e., the loss of normal or sinus rhythm in a heart, and to automatically apply an appropriate therapy to the heart aimed at terminating the arrhythmia. Although there are many therapy protocols that an ICD may follow in its attempt to terminate an arrhythmia, most modern ICD devices provide tiered level therapies in which multiple "tiers" of therapy are utilized. Each "tier" or level of therapy usually corresponds to a different type of arrhythmia, and typically to a specified number of shocks of varying energies and pulse durations intended to most efficiently terminate the specific type of arrhythmia detected.

It is known in the ICD art to provide a tiered therapy with regard to the termination of sensed arrhythmias. Each of the "tiers" of therapy traditionally corresponds to one of a plurality of different arrhythmia "rate zones", corresponding to different arrhythmia rates, such as a low rate ventricular tachycardia (VT Low) rate zone, a high rate ventricular tachycardia (VT High) rate zone, and a ventricular fibrillation (VF) rate zone.

The term "tiered therapy" also has been used to describe different degrees of aggressiveness in each of the therapies delivered in response to arrhythmias detected in each rate zone. For example, within each rate zone a physician or other practitioner may program a tier of therapy having a number of stimulation pulses, a prescribed interval between each of the stimulation pulses, an energy level of each of the stimulation pulses, and the number of attempts, i.e., the number of times the therapy at a particular tier is to be delivered in the event prior attempts are unsuccessful at resolving the arrhythmia, and other similar parameters. Should a particular tier of therapy be unsuccessful after the prescribed number of attempts have been made, a successive, i.e., higher, tier of therapy is applied that is more aggressive (e.g. employs higher energy shocks, etc.). Thus, based upon the detected rate of the arrhythmia, an ICD employing tiered level therapy selects an initial tier of therapy and continues to increase the tier, i.e., level of aggressiveness of the therapy, until such therapy is successful at terminating the arrhythmia. Thus, a principle characteristic of a therapy scheme provided by a tiered-therapy ICD device is that of detecting an arrhythmia and responding by selecting and delivering a programmed therapy of a tier appropriate to the arrhythmia detected; and further, if the programmed therapy selected is unsuccessful at terminating the arrhythmia, increasing the tier, i.e., the aggressiveness, of the therapy over time until the tier of therapy selected is successful.

For example, upon detecting a low rate ventricular tachycardia (VT low), a typical ICD device may attempt to terminate such tachycardia by first applying a tier of therapy for a prescribed type of antitachycardia ("antitach") pacing. Such antitach pacing typically includes burst pacing, ramp pacing, and/or scanning pacing, as is known in the art. See, e.g., U.S. Pat. Nos. 4,427,011 and 4,541,430 (burst pacing); 4,398,536 (ramp pacing); and 5,103,822 (scanning pacing); all of which are incorporated herein by reference. If the tier of therapy for antitach pacing is unsuccessful, the ICD may be programmed to apply a higher tier of therapy in which a low energy, cardioversion energy shock is delivered in an attempt to cardiovert the heart. If the higher tier of therapy is unsuccessful, the ICD may apply an even higher tier of therapy that prescribes a higher energy shock in an attempt to cardiovert the heart. If the tachycardia accelerates to ventricular fibrillation, the system may then apply yet a higher tier of therapy in which a high energy defibrillation shock is applied to the heart, with starting energy values typically on the order of 10 joules and increasing up to 40 joules.

It should be noted that for purposes of the present invention the basic difference between cardioversion and defibrillation is the type of arrhythmia being detected. That is, the term "cardiovert" or "cardioversion" refers to the application of energy shock treatment to a heart in response to a sensed ventricular tachycardia in an attempt to terminate the tachycardia. The term "defibrillate" or "defibrillation," on the other hand, refers to the application of energy shock treatment to a heart in response to a sensed ventricular fibrillation in an attempt to terminate the fibrillation.

Cardioversion is often thought of as being "low energy" since the heart has been known to successfully convert the arrhythmia, i.e., return to sinus rhythm, with electrical shocks in the energy range of from 0.1 to 10 joules. However, if the arrhythmia is a ventricular tachycardia, it is still classified as cardioversion even if the energy required to convert the arrhythmia goes up to a maximum value (e.g., 40 joules).

Defibrillation, on the other hand, is often thought of as being "high energy" since the heart is typically successfully defibrillated with energy shocks in the range of 10 to 40 joules.

In contrast to cardioversion and defibrillation, the pulses that are typically applied to a heart during normal pacing, or antitach pacing, are typically of much lower energy (e.g., between 50 and 200 microjoules).

Unless specifically stated otherwise, as used herein, the term "arrhythmia" is used to refer to all types of heart rhythm abnormalities, i.e., low rate ventricular tachycardia (VT Low), high rate tachycardia (VT High), and ventricular fibrillation (VF). Further, as used herein, the term "cardiovert" or "cardioversion" is used to refer to the application of moderate energy shock treatment (e.g., electrical pulses of between 0.1 and 10 joules) to a heart undergoing a tachyrhythmia in an attempt to terminate such tachyrhythmia. The term "defibrillate" or "defibrillation," on the other hand, is used to refer to the application of high energy shock treatment (e.g., electrical pulses of between about 10 and 40 joules) to a heart undergoing tachyrhythmia or fibrillation in an attempt to terminate such tachyrhythmia or fibrillation.

The therapy delivered, whether cardioversion or defibrillation, is delivered to the heart via an electrode system commonly referred to as "defib leads," "defibrillation leads or electrodes," or "patch electrodes." However, the electrode system could also be epicardial or endocardial (attached to the internal surface of the heart) or patch (attached to the external surface of the heart), or any combination of patch, epicardial or endocardial. Such electrodes are well known in the art. See, e.g., U.S. Pat. No. 4,662,377 (Heilman et al.), issued May 5, 1987, entitled "Cardioverting Method and Apparatus Utilizing Catheters and Patch Electrodes"; U.S. Pat. No. 4,481,953 (Gold et al.), issued Nov. 13, 1984, entitled "Endocardial Lead Having Helically Wound Ribbon Electrode"; and U.S. Pat. No. 4,010,758 (Rockland et al.), issued Mar. 3, 1977, entitled "Bipolar Body Tissue Electrode," all of which are incorporated herein by reference. Hereinafter, the electrode system (whether patch, epicardial, endocardial, etc.) will be referred to as simply "electrodes."

Typically, in order to apply an electrical pulse to the heart (whether of low, moderate, or high energy), it is first necessary to charge one or more output capacitors of the ICD device with an electrical charge of the desired energy. Appropriate electrodes are then coupled to such output capacitor(s) through an appropriate output switch. When an electrical stimulation pulse is to be applied to the heart, the appropriate output switch is closed to connect the output capacitor(s) to the cardiac tissue through either the pacing or shocking electrodes, thereby effectively "dumping" the charge stored in the output capacitor(s) across the cardiac tissue.

In a typical tiered therapy ICD device, each tier of therapy is programmed to provide one or more shocks of a specified energy value. Typically, as explained above, the shock energies corresponding to a given tier of therapy are greater for higher rate zones, e.g., ventricular fibrillation, than for lower rate zones, e.g., low rate tachycardia.

When shock therapy is successively applied during an arrhythmia episode, a general rule followed by all known tiered therapy ICD devices is that the shock energy should be increased from one shock to the next, and never decreased. The only exception to this rule is if the shock energy is already at a maximum level, in which case successive maximum level shocks can be delivered.

One problem with prior art tiered therapy ICD devices is that the above-cited general rule cannot always be followed. For example, when a high rate arrhythmia detection is subsequently followed by a lower rate arrhythmia redetection, then the high rate detection (corresponding to a high rate zone) results in the delivery of a high energy shock (e.g., 10 joules), yet the lower rate arrhythmia redetection (corresponding to a lower rate zone) may result in the delivery of a low energy shock (e.g., 1 joule), even though the prior shock was of higher energy. This departure from the general rule (that successive shocks should always be of increasing value) leads to suboptimal therapy being delivered to the patient.

Another problem with prior tiered therapy ICD devices is that there can be a delay in the delivery of therapy. Typically, a number of detections must occur in a particular rate zone before therapy corresponding to that rate zone is delivered. Unfortunately, in accordance with prior systems, this means that if, for example, four detections in a particular rate zone are required before therapy is delivered, as many as seven such detections may be necessary before therapy is delivered. For example, if three detections are made in a higher rate zone, followed by three detections in a lower rate zone, no therapy will be signaled in either of such rate zones even though a total of six arrhythmia detections have occurred (because four detections have not occurred in either of the rate zones). It is only after one more detection occurs in one of these two rate zones that corresponding therapy will be delivered. As will be appreciated, this problem is compounded when detection is spread across more than two rate zones. This delay in the delivery of therapy inherent in prior tiered therapy ICD devices further results in the delivery of suboptimal therapy to the patient.

Thus, what is needed is an ICD device that delivers tiered therapy wherein the tier of therapy delivered is always increased from one redetection to the next, and wherein the tier of therapy delivered is never decreased; the only exception to this rule being when the last tier of therapy delivered is already at a maximum level in the highest rate zone. What is further needed is an ICD device that delivers tiered therapy wherein subsequent therapy delivery occurs in a timely manner when a particular therapy delivery is unsuccessful.

SUMMARY OF THE INVENTION

The present invention addresses the above and other needs by providing an implantable cardioverter-defibrillator/pacemaker (ICD) device that provides a tiered therapy and furthermore that dynamically readjusts boundaries between rate zones so as to ensure that increasing tiers of therapy are delivered from one redetection to the next in a timely manner.

Since shock energy levels typically increase with each programmed successive tier of therapy within a given rate zone, and also increase from lower rate zones to higher rate zones, one embodiment of the present invention monitors the shock energy that was last delivered within a rate zone. In response to such monitoring, rate zone boundaries are readjusted when such adjustment is needed in order to provide optimal therapy upon subsequent arrhythmia redetections.

In another embodiment of the present invention, an ICD device employing a tiered therapy detects an arrhythmia through an electrode adapted to be coupled to a patient's heart. An output capacitor is coupled to the electrode through an output switch. A charging circuit, coupled to the output capacitor, charges the output capacitor to a programmed energy level. A control circuit, coupled to the charging circuit and to the output switch, generates control signals to control the charging of the output capacitor and the closure of the output switch in accordance with a prescribed tiered therapy. The control circuit dynamically readjusts rate zone boundaries, prior to a subsequent arrhythmia redetection, to include all lower rate zones in a current rate zone. In the event that the last, i.e., greatest energy programmed shock of the current tier of therapy is delivered, the control circuit dynamically readjusts the rate zone boundaries, prior to a subsequent arrhythmia redetection, to include the current rate zone in a higher rate zone unless the current rate zone is the highest rate zone, in which case the last shock of the current rate zone, i.e., the highest rate zone, is repeated upon a subsequent arrhythmia redetection.

In a further embodiment, also including an output capacitor, a charging circuit, an output switch, and a control circuit that controls, inter alia, when the output capacitor is charged, the energy level to which the output capacitor is charged, and when the output switch connects the output capacitor to cardiac tissue through the electrode, the control circuit simply readjusts rate zone boundaries such that delivered shocks within a particular tier of therapy are not repeated (unless the last shock delivered was a maximum energy shock) or followed by shocks of lower energy upon subsequent arrhythmia redetections during a single arrhythmia episode.

An additional embodiment of the present invention may further be characterized as a method of dynamically rezoning rate zone boundaries of an implantable cardioverter defibrillator having tiered therapies corresponding to arrhythmia rate zones. Such method comprises the steps of: (a) detecting/redetecting whether an arrhythmia has occurred; (b) determining, in the event the arrhythmia is detected/redetected in step (a), the rate zone in which the detected/redetected arrhythmia resides, each rate zone having boundaries associated therewith; (c) charging an output capacitor to a programmed level of charge in response to determining the rate zone in step (b); (d) delivering the charge on the output capacitor to a patient through an electrode coupled to the patient's heart; and (e) readjusting the rate zone boundaries, prior to a subsequent arrhythmia redetection, to include all lower rate zones into a current rate zone, and to include a current rate zone in a higher rate zone, in the event that the level of charge of a programmed therapy tier corresponding to the current rate zone has been delivered.

It is thus a feature of the above-described embodiments to provide a tiered therapy ICD that is capable of dynamically readjusting rate-zone boundaries to provide a patient with optimal therapy, i.e., therapy in which each successive shock is of increasing value.

By way of example, when an arrhythmia is detected in a particular rate zone, e.g., a high rate tachycardia rate zone (VT High), all lower rate zones, e.g., a low rate tachycardia rate zone (VT Low), are "pulled up" and included in the current rate zone, VT High. In this way, if a subsequent arrhythmia is redetected in a rate zone that was formerly in the VT Low rate zone, the lower energy shocks corresponding to the tier of therapy normally assigned to the VT Low rate zone will not be delivered. Instead, since the VT Low rate zone is now part of, i.e., included in the VT High rate zone, the ICD device will treat the subsequent arrhythmia redetection as falling within the VT High rate zone. The ICD device will then deliver the next programmed shock assigned to the VT High rate zone. Additionally, if the last programmed shock of the current rate zone (i.e., VT High) has been delivered, the current rate zone is "pushed up" into the next higher rate zone (e.g., the Ventricular Fibrillation rate zone, hereinafter the VF rate zone). Therefore, if a subsequent arrhythmia redetection occurs in what was previously, e.g., the VT High rate zone, the ICD device will treat the redetection as falling within the VF rate zone and deliver the tiers of therapy corresponding to that rate zone. If the current rate zone is the highest programmed rate zone, and the last programmed shock for that rate zone has been delivered, the ICD will repeat delivery of this last programmed shock upon subsequent arrhythmia redetections.

In the manner described above, the ICD device thus ensures that each successive tier of therapy delivered to a patient during a single arrhythmia episode is a higher tier than the previously delivered tier, unless the highest tier of therapy in the highest rate zone has already been delivered, in which case, the highest tier of therapy in the highest rate zone is redelivered upon subsequent arrhythmia redetections.

Furthermore, because typically arrhythmia detections require a plurality of rate averages to accumulate within particular rate zones before such detection is signaled, the ICD device insures that once an arrhythmia is detected in a high rate zone, subsequent rate averages falling in lower rate zones, having been "pulled up" or "pushed up" into the higher rate zone, are counted toward a detection in the higher rate zone. This prevents delays in the delivery of therapy caused by arrhythmias that would otherwise fluctuate between rate zones.

BRIEF DESCRIPTION OF THE DRAWINGS

The above and other aspects, features and advantages of the present invention will be more apparent from the following more particular description thereof, presented in conjunction with the following drawings wherein:

FIG. 2 shows an exemplary electrocardiograph having a P-wave followed by an R-wave (or QRS-complex), and showing an R—R, or ventricular, interval;

FIG. 3 is a rate zone chart showing exemplary definitions of three rate zones, including a range of ventricular intervals (or rate zone boundaries) initially associated with each rate zone;

FIG. 4A is a rate zone chart showing initial rate zone boundaries for the rate zones of FIG. 3;

FIG. 4B is a rate zone chart showing rate zone "pullup" of a VT low rate zone into a VT High rate zone;

Corresponding reference characters indicate corresponding components throughout the several views of the drawings.

DETAILED DESCRIPTION OF THE INVENTION

The following description is of the best mode presently contemplated for carrying out particular embodiments of the invention. This description is not to be taken in a limiting sense, but is made merely for the purpose of describing the general principles of the invention. The scope of the invention should be determined with reference to the claims.

Typically, an arrhythmia is considered to be a rapid irregular rhythm of the heart, e.g., ventricular tachycardia or ventricular fibrillation. However, for purposes of the present application the term arrhythmia also includes atrial tachycardia, atrial fibrillation, and asystole (a stopped heart). Thus, as used herein, the term "arrhythmia" is used broadly to indicate any irregular rhythm of the heart that interferes with the heart's ability to perform its basic function as a pump.

It is the primary function of an implantable cardioverter-defibrillator/pacemaker (ICD) device to sense the occurrence of an arrhythmia, and to automatically apply an appropriate therapy to the heart aimed at terminating the arrhythmia.

Figure 1:
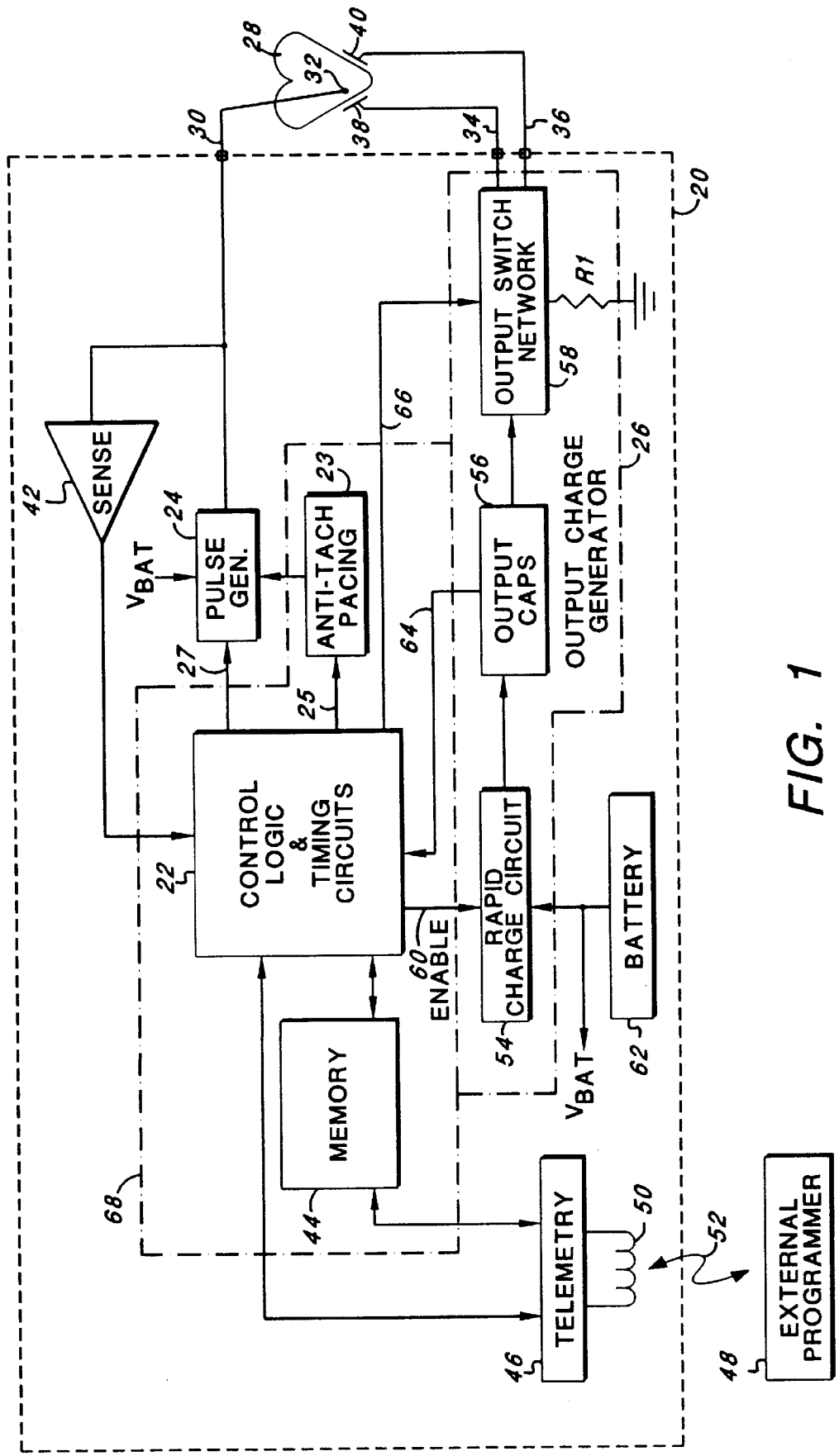
FIG. 1 shows a functional block diagram of an implantable cardioverter-defibrillator/pacemaker (ICD) device that employs tiered therapy, and that dynamically adjusts rate zone boundaries to provide optimal therapy to a patient.

Referring to FIG. 1, a functional block diagram of an ICD device 20 made in accordance with one embodiment of the present invention is shown. The ICD device 20 employs control logic and timing circuits (referred to hereinafter as "control/timing" circuits) 22 that control a pulse generator 24 and a high voltage generator 26. The pulse generator 24 generates output stimulation pulses of low energy (referred to hereinafter as antitach pulses). Such antitach pulses may, for example, be electrical pulses having an energy of less than 1 Joule, as controlled by the control/timing circuit 22 and an antitach pacing circuit 23. The antitach pulses are applied to a patient's heart 28 through a pacing lead 30, such as a pacing lead of the type commonly known in the art, having an electrode 32 in contact with the cardiac tissue (usually inside the right ventricle and/or right atrium). While only a single pacing lead 30 is shown in FIG. 1, it is to be understood that the invention is not so limited, as any number of leads, e.g., two or more, with any number of electrodes, may be used to deliver pacing or antitach pulses to a patient's heart. Use of multiple pacing leads is well known in the art.

The high voltage generator 26 generates output electrical stimulation pulses of moderate or high energy (referred to herein as cardioversion or defibrillation pulses, respectively). For example, the high voltage generator 26 may generate electrical pulses having energies of from 1 to 10 Joules (moderate) or 11 to 40 Joules (high), as controlled by the control/timing circuit 22. Such moderate or high energy pulses are applied to the patient's heart through at least two cardioversion/defibrillation leads 34 and 36, each of which is respectively coupled to a suitable electrode 38 and 40. Typically, the electrodes 38 and 40 of the cardioversion/defibrillation leads are patch electrodes placed in contact with, or near to, external cardiac tissue. The electrodes 38 and 40 may be of conventional design, and may be implanted using known techniques, as shown, e.g., in U.S. Pat. Nos. 4,774,952 (Smits); 4,991,603 (Cohen et al.) and 4,998,975 (Cohen et al.), all of which are incorporated herein by reference. While only two cardioversion/defibrillation leads and electrodes are shown in FIG. 1, it is to be understood that additional leads and electrodes may be used as desired or needed in order to efficiently and effectively apply shock treatment generated by the high voltage generator 26 to the patient's heart 28.

The ICD device 20 also includes a sense amplifier 42 that is coupled to the pacing lead 30 and electrode 32. It is the function of the sense amplifier 42 to sense the activity of the heart 28 as manifest by the presence of certain electrical signals picked up by the electrode 32. That is, R-waves occur upon the depolarization, and hence contraction, of ventricular tissue; and P-waves occur upon the depolarization, and hence contraction, of atrial tissue. Thus by sensing R-waves and/or P-waves through the sense amplifier 42, and providing such sensed signals to the control/timing circuit 22, the control/timing circuit 22 is able to make a determination as to when ventricular and atrial contraction, respectively, have occurred, and thus to make a determination as to the rate and regularity of the cardiac rhythm. Such determination, in turn, allows the control/timing circuit 22 to determine whether the heart 28 is experiencing an arrhythmia.

The control/timing circuit 22 further has a memory circuit 44 coupled thereto wherein the operating parameters used by the control/timing circuit 22 are stored. Such operating parameters may define, for example, the amplitude of the antitach and high voltage stimulation pulses that are to be generated, the type of pattern (e.g., burst, scan and/or ramp) of antitach pulses that are to be used, the timing intervals used to determine whether an arrhythmia is present, and the like. Advantageously, such operating parameters may be non-invasively programmed into the memory 44 through a telemetry circuit 46, in telecommunicative contact with an external programmer 48 by way of a suitable coupling coil 50. The coupling coil 50 may serve as an antenna for establishing a radio frequency (rf) communication link 52 with the external programmer 48; or the coil 50 may serve as a means for inductively coupling data to and from the telemetry circuit 46 from and to the external programmer 48. Further, such telemetry circuit 46 advantageously allows status information relating to the operation of the ICD device 20, as contained in the control/timing circuit 22 or memory 44, to be sent to the external programmer 48 through the established link 52.

The design, operation and use of the telemetry circuit 46 and external programmer 48 to selectively program operating parameters into the memory 44, and/or to selectively monitor the operating status of the ICD 20, may be the same as are known in the ICE/pacing art. See, e.g., U.S. Pat. Nos. 4,809,697 (Causey, III et al.) and 4,944,299 (Silvian), both of which are expressly incorporated herein by reference.

The control/timing circuit 22 includes logic circuits for analyzing the output signals of the sense amplifier 42 and for determining if such signals indicate the presence of an arrhythmia. In one embodiment, an ICD device 20 monitors the four most recent ventricular intervals following a paced or sensed event in order to detect an arrhythmia. The ICD then calculates a rate average of the four most recent ventricular intervals and determines whether this rate average indicates a possible arrhythmia. Rate averaging begins when one ventricular interval falls within a programmed arrhythmia rate zone. Following this one ventricular interval, the next three consecutive intervals are measured and the rate average of the four consecutive intervals, i.e., the rate average of the one ventricular interval and the next three consecutive intervals, is determined.

Although the present embodiment monitors the four most recent ventricular intervals in order to detect arrhythmias, it is apparent that the present invention may be practiced by monitoring fewer or greater than four ventricular intervals, or by monitoring atrial intervals instead of ventricular intervals.

The ventricular intervals are monitored by examining the electrical signals that are manifest concurrent with the depolarization or contraction of ventricular cardiac muscle tissue. The contraction of ventricular cardiac muscle tissue is manifest by the generation of an R-wave (sometimes referred to as a QRS complex). The atrial intervals are monitored by examining the electrical signals that are manifest concurrent with the depolarization or contraction of atrial cardiac muscle tissue. The contraction of atrial cardiac muscle tissue is manifest by the generation of a P-wave. The sequence of electrical signals that represent P-waves, followed by R-waves (or QRS complexes) can be sensed from inside of or directly on the heart by using sensing electrodes implanted inside or on the heart, or by using external electrodes attached to the skin of the patient proximate to the heart. The electrical signals representing P-waves and R-waves sensed internal to or directly on the heart are referred to as the electrogram (EGM) of the heart. The electrical signals representing P-waves and R-waves sensed external to the heart, i.e., at the skin of the patient, are referred to as the electrocardiogram (ECG) of the heart. A skilled cardiologist or other physician can determine a great deal about a patient's heart by simply studying the EGM and/or ECG of the patient. FIG. 2 shows a graphical representation of an electrogram of the heart and depicts the ventricular interval (R—R interval) as the time interval between successive peaks of the "QRS complex".

The ICD device 20 of FIG. 1 uses the sense amplifier 42, the pacing lead 30, and the electrode for sensing P-waves and/or R-waves, and hence for monitoring the patient's EGM. In order to determine the heart rate, for example, the ICD device 20 simply measures the time that elapses between consecutive R-waves. The R-wave is normally used for this determination because the R-wave is usually a much larger signal than the P-wave (because ventricular muscle tissue is much more massive than atrial muscle tissue), and is hence much easier to sense. However, the same rate determination can also be made by measuring the time between consecutive P-waves, if desired.

If an arrhythmia is detected in response to the determination of the rate average, then the control/timing circuit 22 is triggered so as to apply a prescribed tier of therapy corresponding to the rate zone in which the determined rate average lies. The parameters of the prescribed tier of therapy may advantageously be programmed into the memory 44. As shown in FIG. 3, a preferred tiered therapy protocol divides the therapy into three tiers corresponding to three rate zones designated ventricular tachycardia low (VT1 or VT Low), ventricular tachycardia high (VT2 of VT High) and ventricular fibrillation (VF). Each rate zone is defined by a lower cardiac rate limit and an upper cardiac rate limit corresponding to a maximum interval between consecutive detected R-waves, and a minimum interval between consecutive detected R-waves, respectively. The lowest rate zone, VT1, is, in a preferred embodiment, defined by a lowest range of cardiac activity, i.e., cardiac activity in the range of 150 beats per minute (bpm) up to, but not including 200 bpm. The next higher rate zone, VT2, is defined by a next higher range of cardiac activity, i.e., cardiac activity in the range of 200 bpm up to, but not including 240 bpm. The highest rate zone, VF, is defined by a highest range of cardiac activity, i.e., cardiac activity in the range or 240 bpm or higher. For each of these rate zones, a physician may preferably program the energy (and/or other characteristics) of the charges or shocks to be delivered in accordance with each tier of therapy corresponding to each rate zone. In addition, the physician can program the number of charges within each tier of therapy in order to most effectively terminate sensed arrhythmias for each particular patient.

In accordance with the presently-described embodiment, the boundaries of each rate zone are adjustable. The ICD device 20 automatically and dynamically adjusts the rate zone boundaries as necessary in order to deliver optimal therapy to a patient during an arrhythmia episode in accordance with prescribed protocols. Alternatively, a physician may change the rate zone boundaries manually in accordance with the needs of a particular patient.

Referring next to FIGS. 4A thru 4B, changing rate zone boundaries as a result of dynamic rezoning is depicted. FIG. 4A shows the rate zone boundaries described above. If the ICD device 20 initially detects an arrhythmia in the VT High rate zone (i.e., 200 to 240 bpm), the ICD device will deliver the first programmed shock in the VT High rate zone, and then dynamically adjust the rate zone boundaries of the VT High rate zone so that the VT Low rate zone is "pulled up" into the VT High rate zone as shown in FIG. 4-2. In other words, the rate zone boundaries for the VT High rate zone are reset to 150 bpm to 240 bpm. If a subsequent arrhythmia redetection falls in the range of 150 bpm to 200 bpm (formerly the VT Low rate zone), the ICD device 20 will deliver the second programmed shock for the VT High rate zone, instead of delivery of the first programmed shock for the low rate zone, since the VT Low rate zone is now a part of the VT High rate zone. By programming successive shocks for a given rate zone to be of higher energies than prior shocks, delivery of optimal therapy to a patient during an arrhythmia event is realized.

Figure 4C:
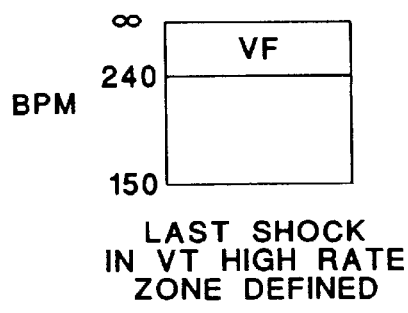
FIG. 4C is a rate zone chart showing rate zone boundaries following delivery of the highest level of shock in the highest (i.e., most aggressive) tier of therapy.
Figure 4D:
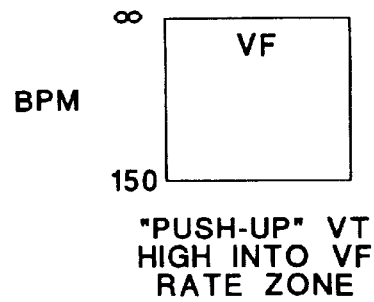
FIG. 4D is a rate zone chart showing rate zone "pushup" of the VT High rate zone into a VF rate zone.

Referring to FIG. 4C, if the last programmed shock of the VT High rate zone has been delivered, the ICD device 20, in accordance with one embodiment of the present invention, then dynamically adjusts the rate zone boundaries such that the VT High rate zone is "pushed up" into the next higher rate zone, i.e., the VF rate zone, as shown in FIG. 4D. This "pushing up" is achieved by setting the rate zone boundaries for the VF rate zone to 150 bpm or above. Therefore if an arrhythmia is subsequently redetected in the range of 150 bpm to 240 bpm (formerly the VT High rate zone), the ICD device 20 will not repeat delivery of the last programmed shock in the VT High rate zone nor cycle back to the first programmed shock in the VT High rate zone, but rather will deliver the first programmed shock within the tier of therapy which is of greater energy than the last programmed shock of the VT High rate zone. Thus, in this way, the ICD device 20 ensures that the patient will receive optimal therapy upon subsequent arrhythmia redetections.

The sorting and storing of rate averages is accomplished by the use of counters within the control/timing circuits 22 (FIG. 1) of the ICD device 20 of FIG. 1. Rate averages that are at a rate greater or equal to the lowest programmed rate threshold, e.g., of the VT low rate zone, are sorted into respective rate zones. The counters accumulate the number of rate averages that have occurred within each rate zone and are therefore denoted "rate-bins". Thus, each rate average falling in a rate zone is accumulated in a rate-bin corresponding to the rate zone. Preferably, for each rate zone, the number of accumulated counts required before delivery of therapy is programmable.

During arrhythmia classification, a termination counter is incremented each time a rate average is detected below the lowest programmed zone threshold. If the termination counter counts a specified number, e.g., six, of consecutive rate averages below the lowest programmed rate zone threshold, the arrhythmia will be classified as terminated. A detected rate average above or equal to the lowest programmed zone threshold causes the termination counter to reset. Therefore, an arrhythmia is classified as terminated only when the specified number of rate averages below the lowest programmed zone threshold occur consecutively.

Figure 5A:
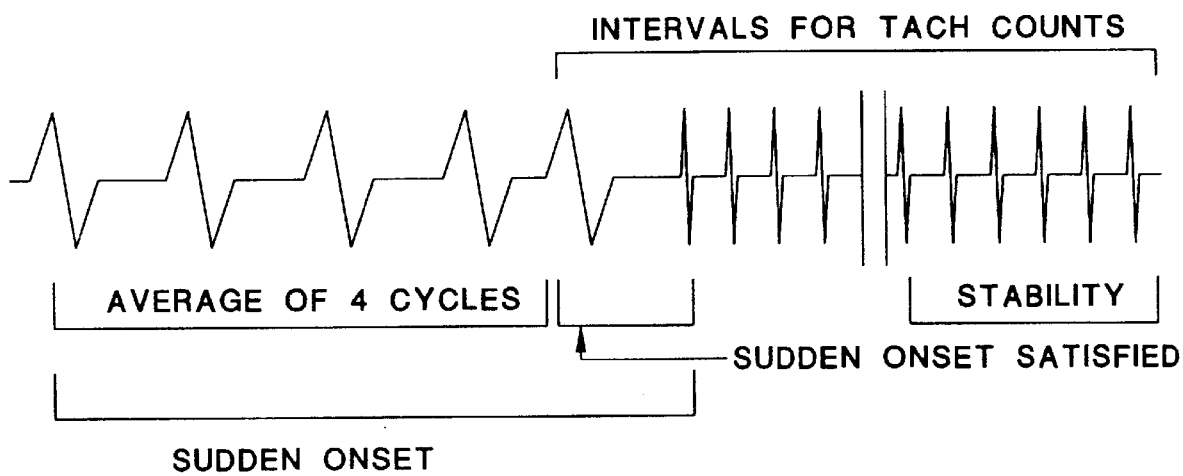
FIG. 5A is an exemplary electrocardiograph illustrating a cardiac activity sequence indicative of sudden onset tachycardia, and a return to stable cardiac function.
Figure 5B:
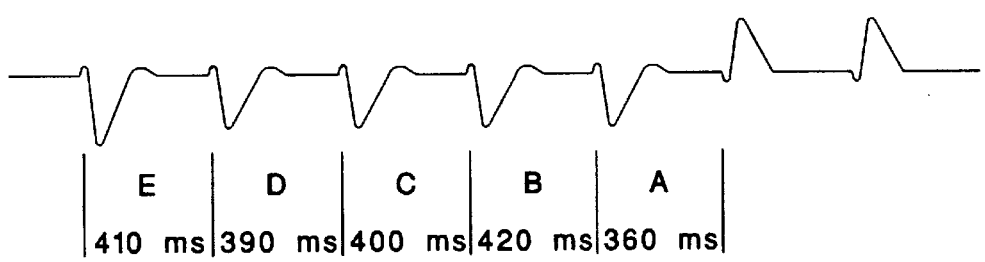
FIG. 5B is an exemplary electrocardiograph illustrating sudden onset tachycardia detection criterion.

Referring to FIG. 5A, in a preferred embodiment, before an arrhythmia is detected by the ICD device 20, a further requirement, referred to herein as the Sudden Onset Criterion, must be satisfied. It is well known in the ICD art that common to all arrhythmias is a sudden increase of heart rate, not a gradual increase. The use of the Sudden Onset Criterion prevents an ICD device 20 from classifying, for example, exercise-induced, gradually accelerated heart rates as an arrhythmia. Patients experiencing normal accelerated heart rates as a result of exercise, therefore, are not given therapy by mistake. FIG. 5B illustrates the application of the Sudden Onset Criterion. As seen in FIG. 5B, interval A (the most recent) is compared, in accordance with the Sudden Onset Criterion, to preceding intervals. To satisfy the Sudden Onset Criterion both of the following conditions must be met:

1. Interval A must be shorter than a programmable percentage of the average of intervals B, C, D, E; and
2. Interval A must be shorter than or equal in duration to the interval defined by the lowest programmed zone threshold.

The Sudden Onset Criterion must be satisfied prior to other enabled detection criteria. Sudden Onset remains satisfied until:

1. Arrhythmia termination criteria are satisfied (e.g., six consecutive rate averages below the lowest programmed rate zone threshold), and
2. For example, eight consecutive non-arrhythmia intervals elapse immediately following satisfaction of the termination criteria, i.e., eight consecutive rate averages below the lowest programmed rate zone threshold.

Referring again to FIG. 1, tiered therapy is implemented by generating, in a controlled time sequence, a series of control signals that activate various elements or features of the embodiment of FIG. 1. For example, a first control signal, appearing on a signal line 25, enables the antitach pacing circuit 23. A second control signal, appearing on a signal line 27, triggers the pulse generator 24 to deliver the antitach pacing defined by the antitach pacing circuit 23 at a controlled time within the cardiac cycle. (The "cardiac cycle" is the time for one complete heart beat, and includes the depolarization of the atrium and the depolarization of the ventricle.) The antitach pacing circuit 23 defines a selected type of antitach pacing, e.g., burst pacing, ramp pacing, or scan pacing, that is delivered to the heart at a time controlled by the antitach pacing control signal 27.

Similar control signals generated by the control/timing circuit 22 control the operation of the high voltage generator 26. As seen in FIG. 1, the high voltage generator 26 includes a rapid charge circuit 54, one or more output capacitors 56, and an output switching network 58. When the control/timing circuits 22 determine the need for a moderate or high energy output pulse, an enable signal 60 enables the rapid charge circuit 54 so that it begins to charge the output capacitor 56 using power derived from a battery 62. As the output capacitor 56 is thus charged, it is monitored via a signal line 64 to determine if the charge (voltage) stored thereon is at a prescribed level defined by a charge level signal programmably stored in the memory 44. (In the present embodiment, the charge level signal is defined by the tier of therapy to be delivered as a function of the rate zone in which the arrhythmia is detected. It will be understood in accordance with other embodiments, however, by the skilled artisan that other parameters, either in addition to or instead of the charge level signal may be defined by the tier of therapy to be delivered. Such other parameters may include the pulse repetition rate, the pulse duration or width, or other such parameters.)

In accordance with the present embodiment, once a prescribed charge level indicated by the charge level signal has been reached, which may take several seconds depending upon the charge level indicated, the output capacitor 56 stands ready to discharge the energy stored in the output capacitor through the output switching network 58 to the heart 28. Another control signal 66 controls the output switching network 66 so as to cause the energy stored on the output capacitor 56 to be delivered.

The control/timing circuits 22, as well as the antitach circuit 23, may be implemented using conventional logic circuitry, i.e., registers and logic gates, configured, e.g., in a suitable state machine. The use of state machine logic circuitry to control an implantable medical device is described, e.g., as shown in U.S. Pat. No. 4,712,555 (Thornander et al.), incorporated herein by reference.

Alternatively, the control/timing circuit 22, antitach pacing circuit 23, and memory circuitry 44 may be implemented using a microcontroller or microprocessor 68. In such instance, an operating program is stored in the memory 44 to control the operation of the microprocessor 68. Typically, such operating program is permanently stored in read only memory (ROM) included as part of the memory 44 of the microprocessor 68, while certain operating parameters or variables associated with the operating program may be downloaded from the external programmer 48 to a random access memory (RAM), also included as part of the memory 44. The use of a microprocessor 68 to control an implanted medical device is described, e.g., in U.S. Pat. No. 4,940,052 (Mann et al.), incorporated herein by reference.

The pulse generator 24 of FIG. 1 may be of conventional design, such as is described in U.S. Pat. No. 4,739,437 (Morgan), incorporated herein by reference. The pulse generator 24 includes an output capacitor (or pulse capacitor) on which a specified charge (voltage) is stored. Such output capacitor is different from the output capacitors 56 included as part of the output charge generator 26. Typically, because the charge (voltage) stored on the output capacitor of the pulse generator 24 must be greater than the voltage available from the battery 62 included with the ICD device 20, a charging circuit is employed as part of the pulse generator 24 to "pump" up the voltage from the battery 62 to a specified voltage stored on the pulse generator output capacitor. When the stimulation pulse is to be generated, the pulse generator is enabled and the electrode 32 is connected to the output capacitor via the implantable lead 30, thereby "dumping" the charge held on the output capacitor through the implantable lead 30 and electrode 32 to desired cardiac tissue.

Figure 6A:
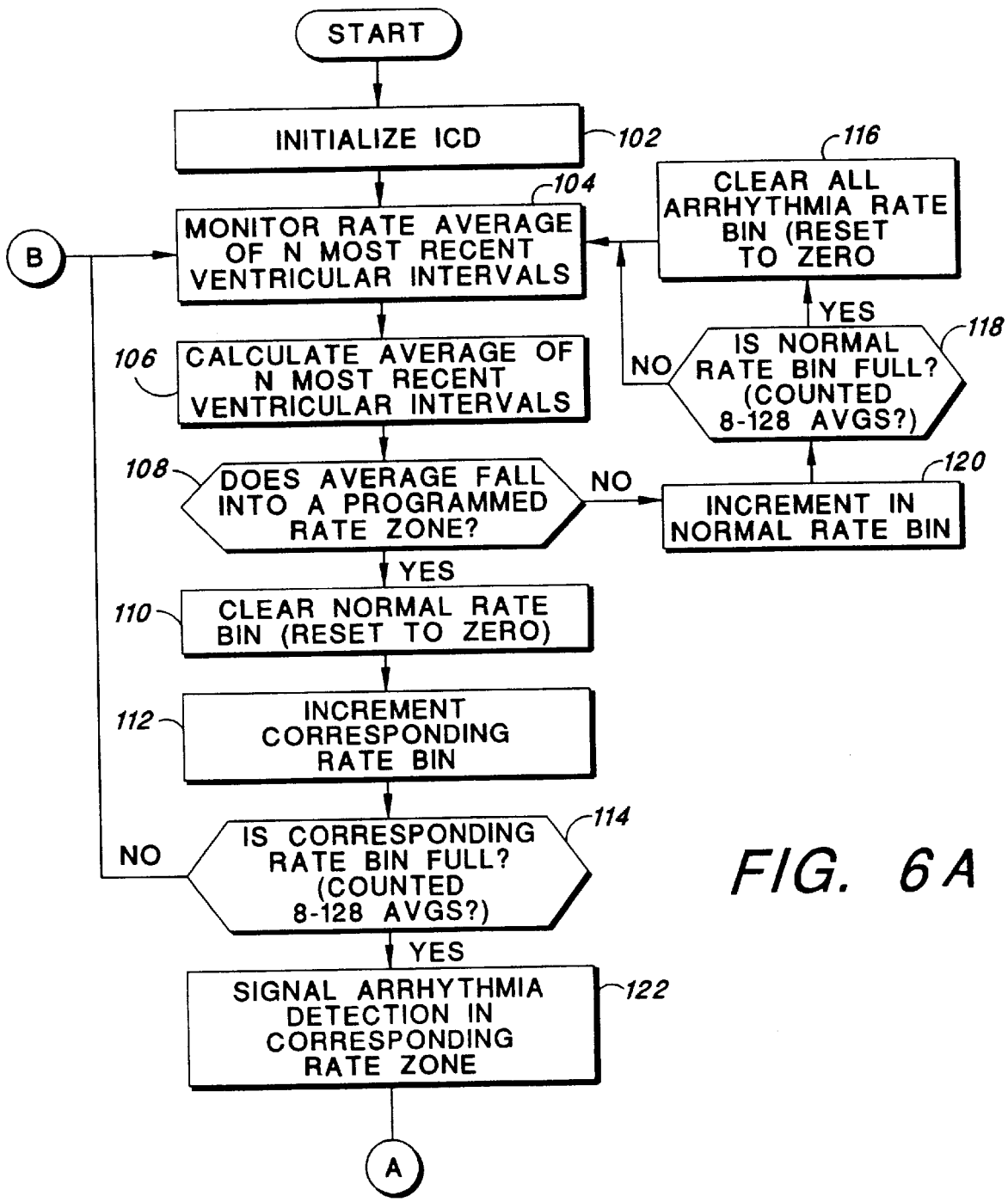
FIG. 6A and 6B are a flow diagram illustrating steps traversed by the ICD device of FIG. 1 in accordance with one embodiment of the present invention.
Figure 6B:
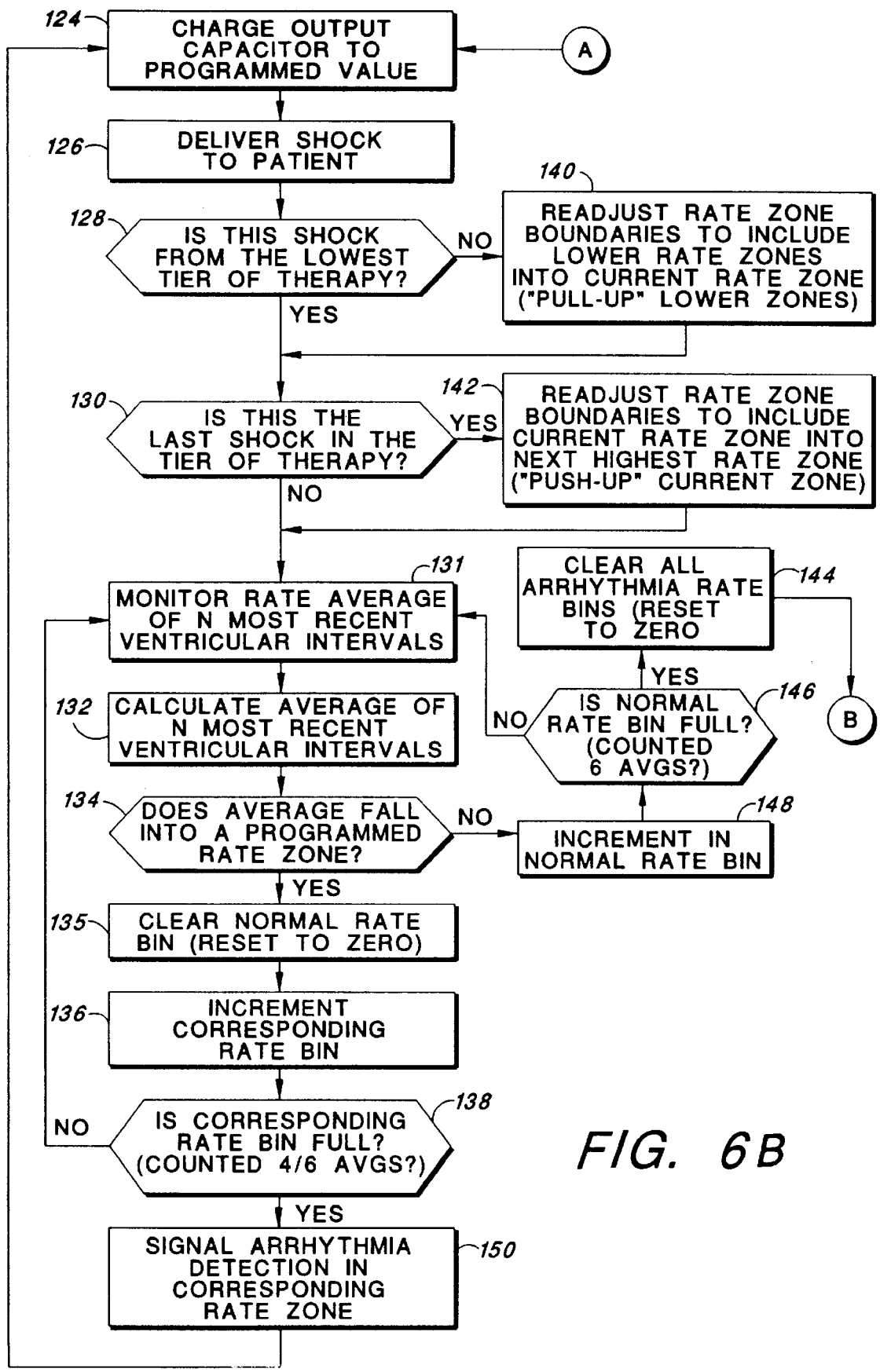

Referring next to FIGS. 6A thru 6B, there is shown a flow diagram that illustrates the operation of the ICD device of FIG. 1 in order to dynamically adjust rate zone boundaries corresponding to programmed tiered therapies in accordance with the present embodiment.

As depicted in FIGS. 6A and 6B, the first step in implementing the dynamic rezoning protocol of the present embodiment is to initialize (Block 102) the ICD device 20. Such initialization involves retrieving all the requisite operating parameters from the memory 44, or equivalent storage device, or otherwise setting all the necessary operating parameters needed to carry out the operation. Such operating parameters define, for example, the type of the antitach pacing to be applied, the energy of the stimulation pulses to be used in antitach pacing, the number of times antitach pacing is to be applied as first tiers in the tiered therapy before stepping up to the next tier in the tiered therapy, the energy of the cardioversion pulses, the number of cardioversion pulses to be applied as second tiers in the tiered therapy before stepping up to the next tier in the tiered therapy, the energy of the defibrillation pulses to be used, and the like.

Once initialization (Block 102) has been completed, the ICD device 20 enters its normal operating mode (Block 104). In the normal operating mode the ICD device 20 monitors (Block 104) ventricular intervals in order to detect arrhythmias. Rate averaging begins when a ventricular interval falls within one of the programmed arrhythmia rate zones, i.e., has a duration shorter than at least a lower rate boundary of the lowest rate zone. Following detection of the ventricular interval within one of the programmed arrhythmia rate zones, the next three consecutive ventricular intervals are averaged (Block 106) with the ventricular interval within the programmed arrhythmia rate zone (regardless of whether the next three consecutive ventricular intervals are within the programmed arrhythmic rate zone) to determine a rate average.

The ICD device 20 next determines (Block 108) whether the determined rate average falls within one of the programmed arrhythmia rate zones. If it is determined that the rate average falls within one of the programmed rate zones (Block 108), the ICD device 20 clears (Block 110) a normal-heart-rhythm rate bin (normal rate bin). (The normal rate bin is incremented each time a rate average indicating a normal heart rhythm (i.e., a normal rate average) is detected by the ICD. If the normal rate-bin "stores" a specified number of consecutive normal rate averages before an arrhythmia is detected, any counted detections of previous rate averages indicating an arrhythmia are cleared (i.e., zeroed), and the ICD device 20 signals termination of the arrhythmia.)

In the event it is determined that a rate average does fall within a programmed arrhythmia rate zone (Block 108), after the ICD device 20 clears (Block 110) the normal rate-bin, the ICD device 20 then "stores" (Block 112) the rate average in a rate-bin corresponding to the arrhythmia rate zone within which the rate average falls. As mentioned above, the rate-bin is simply a counter that is part of the control/timing circuits 22 (FIG. 1). The corresponding rate bin is incremented each time a rate average falls within the corresponding rate zone.

The ICD device 20 then determines (Block 114) whether the corresponding rate-bin is full, i.e., whether the arrhythmia rate-bin corresponding to the rate zone in which the rate average falls has been incremented a specified number of times. Incrementing of the corresponding rate bin the specified number of times renders the corresponding rate-bin full. This specified number may be programmed by a physician or other appropriate person. In a preferred embodiment, the number of rate averages that are counted in a rate-bin before the rate bin is considered full, thus signaling an arrhythmia in the corresponding rate zone, is programmable in the range of 8 to 128.

If it is determined that the rate-bin has not stored the specified number of rate averages (NO branch of Block 114), the ICD device 20 once again resumes monitoring (Block 104) ventricular intervals. And, following detection of a ventricular interval within one of the rate zones, the ICD device 20 determines (Block 106) the average and continues operation as described above (Block 108, et. seq.).

If, following determination of the rate average (Block 106), as described above, it is determined that a rate average does not fall into a programmed arrhythmia rate zone (No branch of Block 108), the normal rate-bin is incremented (block 120). Following incrementing of the normal rate bin, the ICD device 20 determines whether the normal rate-bin is full (block 118), i.e., whether the normal rate-bin has stored a specified number of normal rate averages deemed to indicate a normal heart rhythm or the termination of a previously detected arrhythmia. If it is determined that the normal rate-bin is full (YES branch of Block 118), then the ICD device 20 clears all arrhythmia rate-bins (Block 116), i.e., resets them to zero, and the ICD device 20 once again resumes normal monitoring (Block 104) of the ventricular intervals. Following detection of a ventricular interval within one of the rate zones, the ICD device 20 determines (Block 106) the rate average, and continues operation as described above (Blocks 108, et. seq.).

If, after it is determined that a rate average falls within a programmed arrhythmia rate zone (YES branch of Block 108), and after such rate average is stored in a corresponding rate-bin (Block 112), it is determined that the corresponding rate-bin is full (YES branch of Block 114), the ICD device 20 signals (Block 122) an arrhythmia detection in the corresponding rate zone. The ICD device 20 then determines a charge energy corresponding to a specified tier of therapy prescribed for that corresponding rate zone, and charges (Block 124, FIG. 6B) an output capacitor to the determined charge energy. The ICD device 20 then delivers (Block 126) this charge, i.e., shock, to the patient. Following each delivery of a shock to the patient, the ICD device 20 determines (Block 128) whether the delivered shock came from the lowest rate zone. If it is determined that the last shock delivered was not from the lowest rate zone (NO branch of block 128), the ICD device 20 adjusts (Block 140) rate zone boundaries to include all lower rate zones, i.e., rate zones defined by longer ventricular intervals, into the corresponding rate zone, thereby "pulling up" all lower rate zones into the corresponding rate zone. By "pulling up" all lower rate zones into the corresponding rate zone, the ICD device 20 ensures that a subsequent arrhythmia redetection in a lower rate zone does not result in the delivery of a lower tier of therapy, e.g., lower energy shock, than the last tier of therapy delivered. Instead, since the previously lower rate zone is now a part of the corresponding rate zone (by virtue of having ben "pulled up" into the corresponding rate zone), the ICD device 20 will deliver the next programmed tier of therapy associated with the corresponding rate zone, i.e., the tier of therapy following the last tier of therapy delivered.

The ICD device 20 next determines (Block 130) whether the last shock delivered is the last programmed shock associated with the corresponding rate zone. If it is determined that the last shock delivered is the last programmed shock in the current tier of therapy (YES branch of Block 130), the ICD device 20 readjusts rate zone boundaries for the next higher rate zone (Block 142), i.e., the rate zone above the corresponding rate zone to incorporate the corresponding rate zone into the next higher rate zone, in a sense "pushing up" the corresponding rate zone into the next higher rate zone. By "pushing up" the corresponding rate zone into the next higher rate zone, the ICD device 20 ensures that if a subsequent arrhythmia is detected in the corresponding rate zone, the last tier of therapy, e.g., highest energy tier of therapy, associated with the corresponding rate zone will not be delivered again. Furthermore, by "pushing up" the corresponding rate zone into the next higher rate zone, the ICD device 20 ensures that it will not cycle back to the first tier of therapy associated with the corresponding rate zone, which is most likely of much less energy than the last shock delivered. Instead, if an arrhythmia is redetected in what was the corresponding rate zone, shock energies from the tier of therapy associated with the next higher rate zone are delivered.

The desired general rule for providing optimal therapy requires that during a single arrhythmia episode each successive tier of therapy, e.g., shock, be higher (or more aggressive), e.g., of greater energy, than the previous tier of therapy if the previous tier of therapy has not successfully terminated the arrhythmia. Advantageously, the present embodiment functions in accordance with the above-described general rule. The present system also is free from the time delay problem inherent in prior systems, that results in a delayed delivery of therapy when arrhythmia detections of a single episode occur in more than one rate zone. The time delay problem is overcome because once a detection occurs in a higher rate zone, the lower rate zone is "pulled up" into the higher rate zone, thus making all subsequent rate averages in either rate zone count as events in the higher rate zone.

Following the delivery of therapy (Block 126, FIG. 6A) and the dynamic rezoning process described above (Blocks 128, 140, 130 and 142), the ICD device 20 determines whether the therapy most recently delivered to the patient has terminated the detected arrhythmia. To make such determination, the ICD device 20 again monitors (Block 131) the rate average of the four most recent ventricular intervals, and determines (Block 134) whether this rate average falls into a programmed arrhythmia rate zone. If it is determined that the rate average does not fall within a programmed rate zone (block 134), the ICD device 20 increments (Block 148) the normal rate-bin and then determines (Block 146) whether the normal rate-bin is full.

If it is determined that the normal rate-bin is full (YES branch of Block 146), the ICD device 20 clears all arrhythmia rate-bins, resetting them to zero (Block 144), and signals that the arrhythmia has been terminated. The normal rate-bin is considered full if the specified number of normal rate averages have been counted. As mentioned above, this specified number is programmable and may be prescribed by a physician or other appropriate person.

In a preferred embodiment, if the normal rate-bin counts six consecutive normal rate averages, the ICD device 20 will signal an arrhythmia termination. After a determination that an arrhythmia has been terminated, the ICD device 20 once again monitors (Block 104, FIG. 6A) ventricular intervals for a ventricular interval that falls into one of the rate zones. In response to a detection of a ventricular interval falling in one of the rate zones, the ICD device 20 again determines (Block 106) a rate average of the detected ventricular interval together with the next three consecutive ventricular intervals. Operation of the ICD device 20 then continues (Block 108 et seq.) as described above.

If it is determined (NO branch of Block 146) that the normal rate-bin is not full, the ICD device 20 will continue to monitor (Block 131) the ventricular interval and calculate (Block 132) rate averages, as described above, until it is determined that the arrhythmia has been terminated or redetected.

If it is determined that a rate average falls into a programmed rate zone (YES branch of Block 134), the ICD device 20 clears, i.e., zeros, the normal rate-bin (Block 135). (The normal rate-bin is cleared because a rate average that falls within an arrhythmia rate zone breaks up a sequence of consecutive normal rate averages required to signal an arrhythmia termination, as described above). The ICD device 20 then increments (Block 136) the corresponding arrhythmia rate-bin and determines (Block 138) whether the corresponding rate-bin is full. If it is determined that the corresponding rate-bin in not full (NO branch of Block 138), the ICD device 20 continues monitoring (Block 131) and calculating (Block 132) the rate averages in order to determine the status of the previously detected arrhythmia, i.e., to determine whether the previously detected arrhythmia is terminated or continuing. If it is determined that the corresponding rate-bin is full (YES branch of Block 138), the ICD device signals (Block 150) an arrhythmia redetection in the corresponding rate zone. (Note that rate zone boundaries may have been adjusted at this stage.)

A rate-bin is considered full when it has stored a specified number of rate averages. As described above, this specified number is programmable by a physician or other appropriate person. In a preferred embodiment, the ICD device 20 redetects an arrhythmia when four rate averages are found that are within the lowest rate zone, i.e., the rate zone defined by the longest ventricular intervals, that has available therapy. If there are higher rate zones enabled, the preferred embodiment requires six rate averages that are within the higher rate zone to redetect the arrhythmia in the higher rate zones.

Thus, redetection in the lowest rate zone that has available therapy requires fewer rate averages (e.g., four) in the lowest rate zone than are required in higher rate zones (e.g., six). This disparity eliminates biases inherent in the redetection of arrhythmias. Specifically, when an arrhythmia is initially detected the current rate zone automatically becomes the lowest rate zone that has available therapy due to the "pulling up" of all lower rate zones into the current rate zone. However, while the ICD device is preparing to deliver therapy to the patient (e.g., charging the output capacitor), the ICD device 20 does not monitor rate averages falling into the current rate zone. The ICD device 20 does, however, continue to collect and store rate averages which fall into higher rate zones. Therefore, because when a patient is undergoing an arrhythmia episode it is very common that the patient's heart rate is rapidly varying between two rate zones, and furthermore because rate-bins corresponding to higher rate zones continue to collect rate averages falling within the higher rate zones, while the lowest (current) rate zone is not collecting such rate averages, subsequent arrhythmia redetections are biased towards the higher rate zones.

This bias toward higher rate zones means that an arrhythmia varying between two rate zones will tend to favor detection of an arrhythmia in a higher rate zone instead of the current rate zone and therapy will thus be skewed toward higher tiers of therapy, e.g., higher energy shocks, corresponding to the higher rate zone. This bias, however, is contrary to the notion of tiered therapy in which the goal is to provide the lowest energy shock with a good chance of terminating a sensed arrhythmia and to gradually increase the aggressiveness of the therapy, i.e., the energy of the shock. Hence, requiring a fewer number of rate averages for redetection of a arrhythmia in the current (i.e., lowest) rate zone than are required to redetect an arrhythmia within a higher rate zone, not only eliminates the bias toward redetection in higher rate zones, but results in therapy being delivered at the lowest tier with a reasonable chance of terminating a sensed arrhythmia being administered.

After it has been determined (YES branch of Block 138) that the corresponding rate-bin is full and the ICD device 20 has signaled (Block 150) an arrhythmia redetection, the ICD device 20 then charges (Block 124) the output capacitor to a programmed value in accordance with a tier of therapy associated with the corresponding rate zone, and then delivers (Block 126) this shock to the patient. The ICD device 20 then performs (Blocks 128, 140, 130 and 142 and Blocks 131, et seq.) the same rezoning and redetection protocols as described above.

In a preferred embodiment, the following Shock Section Criteria is used when it is necessary to select and give another shock, after an unsuccessful shock, from the available programmed shocks:

1. If the detected rate zone has not changed, the next shock from the detected zone is selected. If no more shocks are available in a rate zone, redetection is not possible in that zone because such zone will have been "pushed up".
2. When shock therapy advances to a higher rate zone due to exhaustion of shocks within a rate zone or acceleration into a higher rate zone, only a shock which is at a higher energy than the previous shock energy is selected from programmed shock energies in the tier of therapy for the higher rate zone, provided the previous shock was not already at a maximum programmed energy.
3. If the previous shock was already at the maximum programmed energy, then the next programmed shock of the same energy is selected.

4. If therapy advances to a tier of therapy associated with VF rate zone and the first shock energy of the VF shock sequence is not the first programmed shock energy, the total number of possible VF shocks remains as programmed, e.g., five, with the additional available shocks at an energy equal to the third through fifth VF shocks.

5. When all of the VF shock therapy has been delivered, no more shocks are possible until termination is detected and a new episode has begun.

6. If the arrhythmia rate zone advances to a higher zone during charging, the ICD device 20 selects the first shock in the new rate zone that is of equal or higher energy than the shock that was preempted by the rate-zone advance.

As described above, it is thus seen that the present invention provides a tiered-therapy ICD device 20 that advantageously provides for dynamically adjusting rate zone boundaries in order to ensure that prior shocks are always followed by shocks of higher energy, unless the last shock delivered was the maximum energy shock available in the ICD device 20, in which case such shock is repeated upon subsequent arrhythmia redetections.

While the invention herein disclosed has been described in specific embodiments and applications thereof, numerous modifications and variations could be made thereto by those skilled in the art without departing from the scope of the invention set forth in the claims.

What is claimed is:

1. An implantable cardioverter defibrillator/pacemaker (ICD) delivering tiered level therapies corresponding to hierarchical arrhythmia rate zones, the ICD comprising:

at least one electrode for coupling to a patient's heart;

a sensing circuit for detecting an arrhythmia through the at least one electrode;

an output switch coupled to the at least one electrode;

an output capacitor coupled to the at least one electrode through the output switch;

a charging circuit, coupled to the output capacitor, for charging the output capacitor to a programmed energy level; and a control circuit, coupled to the sensing circuit, the charging circuit and the output switch, for determining a current rate zone in which the detected arrhythmia falls and for generating control signals to control the charging of the output capacitor and closure of the output switch in accordance with a prescribed tiered therapy corresponding to the current rate zone, the control circuit further comprising:

means for defining a plurality of rate zones, each rate zone having rate zone boundaries associated therewith, and each having a prescribed tiered therapy associated therewith, wherein each tiered level therapy includes a preprogrammed number of shocks including a last shock of greatest energy;

means for dynamically readjusting the rate zone boundaries of the current rate zone prior to a subsequent arrhythmia redetection to include all lower rate zones into the current rate zone; and means for dynamically readjusting the rate zone boundaries to include the current rate zone in a higher rate zone in the event that the last shock of a tiered level of therapy for the current rate zone is delivered.

2. The ICD, as defined in claim 1, wherein the control circuit further comprises:

means for measuring a prescribed number of most recent ventricular intervals of a patient's heart, where the prescribed number is an integer greater than one;

means for calculating a rate average of the prescribed number of most recent ventricular intervals;

means for sorting and storing the rate average according to a corresponding rate zone within which the rate average falls, the corresponding rate zone corresponding to a programmed tier of therapy;

means for checking if a programmed number of rate averages corresponding to a particular rate zone have been stored, where the programmed number is an integer greater than one; and means for signaling, in the event the programmed number of rate averages have been stored, an arrhythmia detection/redetection in the corresponding rate zone.

3. The ICD, as defined in claim 2, wherein the means for sorting and storing rate averages comprises a plurality of rate-bins, each rate-bin corresponding to an arrhythmia rate zone, and wherein the means for checking comprises means for determining whether a particular rate-bin has stored the programmed number of rate averages.

4. The ICD, as defined in claim 2, wherein the means for checking includes:

means for determining whether the programmed number of rate averages corresponding to the particular rate zone have been counted; and means for determining whether another number of rate averages corresponding to another rate zone have been counted, the other number being less than the programmed number and the other rate zone being a lower rate zone than the particular rate zone.

5. The ICD, as defined in claim 1, wherein the control circuit comprises a microprocessor.

6. An implantable cardioverter defibrillator/pacemaker having tiered level therapies corresponding to hierarchical arrhythmia rate zones, wherein the tiered levels correspond to arrhythmia rate zones, each rate zone having rate zone boundaries, the implantable cardioverter defibrillator/pacemaker comprising:

an electrode for coupling to a patient's heart;

means coupled to the electrode for detecting an arrhythmia through the electrode;

means for determining a current rate zone into which the detected arrhythmia falls;

an output switch coupled to the electrode;

an output capacitor coupled to the electrode through the output switch;

charging means, coupled to the output capacitor, for charging the output capacitor to a programmed energy level;

control means, coupled to the charging means and the output switch, for generating control signals to control the charging of the output capacitor and the closure of the output switch in accordance with a prescribed tiered therapy, wherein the prescribed tiered therapy corresponds to a prescribed arrhythmia rate-zone, wherein each tiered therapy includes a preprogrammed number of shocks including a last shock of greatest energy; and means for dynamically readjusting rate zone boundaries of the current rate zone, prior to a subsequent arrhythmia redetection, to pull up all lower rate zones into the current rate zone and, in the event that the last shock of a tiered therapy corresponding to the current rate zone has been delivered, to push up the current rate zone into a higher rate zone.

7. The implantable cardioverter defibrillator/pacemaker as defined in claim 6, wherein the means for detecting an arrhythmia comprises:

means for measuring a prescribed number of most recent ventricular intervals of a patient's heart, where the prescribed number is an integer greater than one;

means for calculating a rate average of the prescribed number of most recent ventricular intervals;

means for sorting and counting the rate average according to a programmed rate zone within which the rate average falls, the programmed rate zone corresponding to a programmed tier of therapy; and means for checking if a programmed number of rate averages corresponding to a particular rate zone have been counted;

means for signaling, in the event the programmed number of rate averages have been counted, an arrhythmia detection in the corresponding rate zone.

8. The implantable cardioverter defibrillator/pacemaker as defined in claim 7, wherein the means for sorting and counting rate averages comprises a plurality of rate-bins, each rate-bin corresponding to an arrhythmia rate zone, and wherein the means for checking comprises means for determining whether a particular rate-bin has counted the programmed number of rate averages.

9. The implantable cardioverter defibrillator/pacemaker as defined in claim 7, wherein the means for checking includes:

means for determining whether the programmed number of rate averages corresponding to the particular rate zone have been counted; and means for determining whether another number of rate averages corresponding to another rate zone have been counted, the other number being less than the programmed number and the other rate zone being a lower rate zone than the particular rate zone.

10. The implantable cardioverter defibrillator/pacemaker as defined in claim 6, wherein the control circuit comprises a microprocessor.

11. A method of dynamically rezoning the rate zone boundaries of an implantable cardioverter defibrillator/pacemaker having tiered therapies corresponding to hierarchical arrhythmia rate zones, the method comprising the steps of:

detecting whether an arrhythmia has occurred;

determining a current rate zone in which the detected arrhythmia falls;

charging an output capacitor to a programmed value as a function of the current rate zone determined;

discharging the output capacitor to a patient through an electrode coupled to the patient's heart;

adjusting rate zone boundaries, prior to subsequent arrhythmia redetection, to include all lower rate zones into the current rate zone and, in the event that a last shock of a programmed therapy corresponding to the current rate zone has been delivered, to include a current rate zone in a higher rate zone.

12. The method as defined in claim 11, wherein the determining step comprises the steps of:

measuring a prescribed number of most recent ventricular intervals, where the prescribed number is an integer greater than one;

calculating a rate average rate for the prescribed number of most recent ventricular intervals;

sorting and counting the rate average calculated to a programmed rate zone within which the rate average falls, the rate zone corresponding to a programmed tier of therapy;

evaluating whether a programmed number of rate averages corresponding to a particular rate zone have been stored; and signaling, in the event the programmed number of rate averages have been stored, an arrhythmia detection in the particular rate zone.

13. The method as defined in claim 12, wherein the step of sorting and counting rate averages is accomplished by storing the rate averages in rate-bins, the rate-bins corresponding to programmed rate zones, and wherein the step of signaling includes signaling in the event a particular rate-bin corresponding to the particular rate zone stores the programmed number of rate averages, the arrhythmia detection in the particular rate-zone.

14. The method as defined in claim 11, wherein the evaluating includes:

determining whether the programmed number of rate averages corresponding to the particular rate zone have been counted; and determining whether another number of rate averages corresponding to another rate zone have been counted, the other number being less than the programmed number and the other rate zone being a lower rate zone than the particular rate zone.

15. A method of dynamically rezoning the rate zone boundaries of an implantable cardioverter defibrillator/pacemaker (ICD) the method comprising:

detecting an arrhythmia in a heart;

classifying the arrhythmia into one of a plurality of rate zones, which plurality of rate zones includes lower rate zones and higher rate zones;

delivering a programmed therapy to the heart as a function of the one of the plurality of rates zones into which the arrhythmia is classified;

adjusting rate zone boundaries to include in the one of the plurality of rate zones all lower rate zones; and adjusting rate zone boundaries to include the one of the plurality of rate zones in a higher rate zone, in the event a last programmed therapy corresponding to the one of the plurality of rate zones is delivered.

16. The method as defined in claim 15, wherein the detecting step comprises:

measuring durations of a prescribed number of ventricular intervals, where the prescribed number is an integer greater than one;

calculating an average duration of the prescribed number of ventricular intervals;

sorting the average duration calculated into the one of the plurality of rate zones within which the rate average falls, the rate zone corresponding to a programmed tier of therapy;

counting a number of times the average duration calculated falls into the one of the plurality of rate zones;

repeating the measuring, calculating, sorting and counting steps a multiplicity of times;

evaluating, during the repeating, whether the number of times the average duration calculated falls into the one of the plurality of rate zones reaches a programmed number; and signaling, in the event the number of times reaches the programmed number, an arrhythmia detection in the one of the plurality of rate zones.

17. The method as defined in claim 15, further comprising:

calculating an average ventricular interval of the prescribed number of ventricular intervals, excluding a most recent of the prescribed number of ventricular intervals;

determining whether the most recent of the prescribed number of ventricular intervals is shorter than the average ventricular interval by more than a prescribed amount;

determining whether the most recent of the prescribed number of ventricular intervals is not longer than a lowest programmed rate zone boundary of a lowest rate zone; and the detecting of the arrhythmia in the heart occurring only in the event the most recent of the prescribed number of ventricular intervals is both shorter than the average ventricular interval by more than the prescribed amount, and is not longer than the lowest programmed rate zone boundary of the lowest rate zone.

18. An implantable cardioverter defibrillator/pacemaker (ICD), comprising:

means for delivering tiered level therapies corresponding to hierarchical arrhythmia rate zones including a current rate zone and a higher rate zone, each rate zone having rate zone boundaries associated therewith, wherein each tiered level therapy includes a preprogrammed number of shocks including a last shock of greatest energy; and means for dynamically rezoning the rate zone boundaries such that the current rate zone is included in a higher rate zone after the last shock of greatest energy has been delivered corresponding to the current rate zone.

19. An implantable ICD according to claim 18, further comprising means for redecting an arrhythmia and means for activating the dynamic rezoning means prior to redetection of the arrhythmia.

20. An implantable cardioverter defibrillator/pacemaker (ICD) delivering tiered level therapies corresponding to hierarchical arrhythmia rate zones, each rate zone having rate zone boundaries associated therewith, wherein each tiered level therapy includes a preprogrammed number of shocks including a last shock of greatest energy, the ICD comprising:

a detecting circuit that detects an arrhythmia;

a control circuit, coupled to the detecting circuit, that determines a current rate zone within which the detected arrhythmia falls and control s delivery of the tiered level therapy corresponding to the current rate zone, wherein the control circuit dynamically readjusts the rate zone boundaries to include the current rate zone in a higher rate zone in the event that the last shock of a programmed therapy corresponding to the current rate zone is delivered.

21. A method of dynamically rezoning the rate zone boundaries of an implantable cardioverter defibrillator/pacemaker (ICD) having tiered therapies corresponding to hierarchical arrhythmia rate zones, each rate zone having rate zone boundaries associated therewith, the method comprising the steps of:

detecting an arrhythmia;

determining a current rate zone within which the detected arrhythmia falls;

delivering a tiered therapy corresponding to the current rate zone including delivering a last shock of greatest energy corresponding to the current rate zone; and adjusting rate zone boundaries, after the last shock is delivered and prior to a subsequent arrhythmia redetection, to include the current rate zone in a higher rate zone.

* * * * *